United States Patent [19]

Wristers

[11] 4,036,738
[45] July 19, 1977

[54] HYDROCRACKING IN STRONG ACID SYSTEMS WITH PALLADIUM OR IRIDIUM

[75] Inventor: Jos Wristers, Plainfield, N.J.

[73] Assignee: Exxon Research and Engineering Company, Linden, N.J.

[21] Appl. No.: 577,349

[22] Filed: May 14, 1975

[51] Int. Cl.$^2$ .............................................. C10G 13/08
[52] U.S. Cl. ................................... 208/108; 208/111; 208/112; 252/441; 252/477 R; 260/667
[58] Field of Search ................. 208/108, 111; 260/667

[56] References Cited

U.S. PATENT DOCUMENTS

| | | | |
|---|---|---|---|
| 2,446,998 | 8/1948 | Burk | 208/108 |
| 3,409,684 | 11/1968 | Aristoff et al. | 260/667 |
| 3,847,795 | 11/1974 | Rieve et al. | 208/108 |
| 3,901,790 | 8/1975 | Siskin et al. | 208/108 |

Primary Examiner—Delbert E. Gantz
Assistant Examiner—G. E. Schmitkons
Attorney, Agent, or Firm—Jay Simon; John W. Ditsler

[57] ABSTRACT

Hydrocarbon feedstocks are hydrocracked by contacting the feedstock in the presence of hydrogen and under hydrocracking reaction conditions with a catalyst comprised of a metal fluoride, the metal being tantalum, niobium, boron or mixtures thereof, a fluoride containing Bronsted acid and palladium or iridium, the Bronsted acid being present in at least an equimolar amount relative to the metal fluoride and sufficient to dissolve at least a portion of the metal fluoride. The presence of palladium or iridium serves to extend the hydrocracking catalyst life of the metal fluoride and fluoride containing Bronsted acid. The catalyst can be described as a slurry or dispersion composed of the noble metal on a support in a liquid phase acid system.

14 Claims, No Drawings

HYDROCRACKING IN STRONG ACID SYSTEMS WITH PALLADIUM OR IRIDIUM

CROSS REFERENCE TO RELATED APPLICATION

This application is related to copending U.S. Patent Application Ser. No. 317,610 filed Dec. 22, 1972, which issued Aug. 26, 1975 as U.S. Pat. No. 3,901,790.

FIELD OF THE INVENTION

This invention relates to an improved hydrocracking catalyst and an improved hydrocracking process. More particularly, this invention relates to a hydrocracking process and catalyst therefor wherein palladium or iridirum is utilized in conjunction with a metal fluoride/fluoride containing Bronsted acid catalyst to enhance the hydrocracking catalyst life ot the metal fluoride/fluoride containing Bronsted acid catalyst.

DESCRIPTION OF THE PRIOR ART

Conventional hydrocracking operations generally employ a catalyst comprising one or more components exhibiting hydrogenation activity either in the elemental form or as the oxide or sulfide. Such components are usually disposed by impregnation of the component on inorganic porous supports, e.g., silica, silica-alumina, crystalline alumino silicates, etc. While such operations are eminently succesful, they suffer certain disadvantages, for example, high hydrogen pressures, e.g. 1,200–2,000 psig, are required to avoid heavy coke deposition on the catalyst (leading to severely reduced catalytic activity) and the intolerance of such catalysts to sulfur containing feedstocks.

In aforementioned U.S. Pat. No. 3,901,790, the disclosure of which is hereby incorporated by reference, it was proposed to hydrocrack hydrocarbon feedstocks with a catalyst comprising a metal halide and a protonic acid capable of donating a proton to the system. Accordng to this invention, the hydrocracking catalyst life of some of the catalyst systems disclosed in U.S. Pat. No. 3,901,790 can be significantly enhanced by adding a supported palladium hydrogenation component to the acid catalyst.

Catalyst systems containing Friedel-Crafts metal halide/hydrogen halide components in conjunction with supported metal hydrogen catalysts have been described in U.S. Pat. No. 3,409,684 as being useful in the partial hydrogenation of condensed polynuclear aromatics. Additionally, catalyst systems wherein a noble metal on a support, e.g., alumina, has been chemically reacted with a Friedel-Crafts halide such as $AlCl_3$ have also been reported in various patents, e.g., U.S. Pat. Nos. 3,022,252; 2,194,461; 2,964,462 and 3,031,419. Nevertheless, it is believed that the particular catalyst system and its use as a hydrocracking catalyst described hereinbelow has heretofore not been disclosed.

SUMMARY OF THE INVENTION

In accordance with this invention, it has been found that a wide variety of hydrocarbon feedstocks, including sulfur containing feedstocks, can be successfully hydrocracked at relatively low temperatures and pressures with a long life catalyst system comprising a metal fluoride, a fluoride containing Bronsted acid capable of donating a proton to the system, and a palladium or iridium hydrogenation component.

Essentially, the hydrocarbon feed is relatively insoluble in the acid catalyst. Thus, when hydrocarbon feeds are brought into contact with the catalyst, the more basic compounds are extracted into the catalyst phase and hydrocracked. The products of the hydrocracking reaction, e.g., paraffins and naphthenes, are then released back into the hydrocarbon phase.

In co-pending application Ser. No. 577,350 filed on the same date herewith it is disclosed that Group VIII noble metals, generally, enhance the hydrocracking catalyst life of the acid catalyst described in U.S. Pat. No. 3,901,790. However, it has also been surprisingly discovered that of the Group VIII noble metal hydrogenation components, palladium and iridium exhibit a vastly increased reaction rate when compared to other Group VIII noble metals.

The make-up of the catalyst system is critically important to the functioning of the catalyst in a hydrocracking mode. Thus, as described in U.S. Pat. No. 3,901,790, the Bronsted acid should be present in sufficient amount to dissolve at least a portion of metal fluoride catalyst component and, based on metal fluoride, the Bronsted acid should be present in a mole ratio of at least 1:1 in the reaction zone. Generally, however, the activity of the acid catalyst system increases as the molar ratio of Bronsted acid to metal fluoride increases (but will ultimately level out as the Bronsted acid dilutes the overall acidity of the reaction system). Thus, the molar ratio of Bronsted acid to metal fluoride is preferably at least about 2:1, more preferably at least about 5:1. The upper limit is not critical since the Bronsted acid may serve as a diluent or solvent for the reaction. Depending on the relative amounts of materials employed this portion of the catalyst will exist as a separate phase in the reaction mixture and at least some portion or all of the metal halide will be dissolved in the Bronsted acid.

Metal fluorides useful in catalyst formation are the fluorides of tantalum and niobium and boron. Often, in the use of tantalum and niobium, these metals are formed in intimate mixtures and, therefore mixtures of tantalum and niobium fluorides may also be employed. Tantalum and niobium are preferred.

The Bronsted acid component of the catalyst should be a fluoride containing compound capable of donating a proton to the system, a protonic acid. Fluoride containing materials are preferred in order to avoid undesirable halogen exchange reactions. Useful acids include hydrogen fluoride, fluorosulfonic acid, trifluoromethane sulfonic acid, and trifluoroacetic acid. The acids may be employed alone or mixed with their corresponding anhydrides. Hydrogen fluoride is normally preferred.

The third component of the catalyst system is a supported palladium or iridium hydrogenation component. Palladium or iridium is known by itself or in conjunction with other materials to hydrogenate unsaturated hydrocarbons. However, in the environment of the present invention, palladium exhibits a markedly superior reaction rate. This result is wholly unexpected in view of the normally expected similarities among Group VIII noble metals, particularly platinum and palladium. The hydrogenation component should be a supported metal or oxide or sulfide thereof.

The hydrogenation component is preferably carried on a solid support which does not react with the acidic components of the catalyst system and is capable of mixing with the acidic component, that is, the hydrogenation component will exist, likely as a dispersion, in the acid catalyst phase rather than in the hydrocarbon phase. Supports that can be used are charcoal, char, carbon, coke, fluorided refractory oxides, Teflon and the like. In this case, such known untreated supports as alumina, silica, titania and other of these refractory oxides are not suitable due to the susceptibility of these materials to attack and degradation by fluorides. A particularly preferred hydrogen active component is palladium on carbon.

The hydrogenation component of the catalyst system is generally commercially available but can be easily prepared by contacting the carbon support with an aqueous palladium salt, evaporating off the water and then reducing with hydrogen for two hours at about 300° C. The supported hydrogenation component may range preferably in particle size from 38 micrometers to 25 millimeters, preferably 75 micrometers to 12.5 millimeters.

The amount of hydrogenation component utilized is not critical but should be sufficient to effect an increase of the catalyst life of the acidic hydrocracking catalyst. Catalyst life begins to be increased at palladium levels at least about 0.0001 wt. % metal hydrogenation component weight %, based on acid, preferably 0.001 and more preferably 0.05 wt. %. Increasing amounts of hydrogenation component servo to simply increase the hydrogenation rate.

The completed catalyst comprises a liquid phase acid containing a supported noble metal. As mentioned, the support should be one that does not react with the acid. The concentration of the noble metal on the support can range from about 0.01 to about 20 wt. % based on the support, preferably about 0.2 to about 10 wt. %. The supported metal constituent can range in particle size from a fine powder, i.e, with diameters from 38 micrometers to 25 millimeters, although particle size is not a critical item of the make-up of the catalyst (it being sufficient only in that the supported metal form a dispersion in the acid phase catalyst). The supported metal increases acid catalyst life when present in only minute amounts, i.e., $1.0 \times 10^{-4}$ wt. %, preferably $1.0 \times 10^{-3}$ wt. %, and more preferably $5 \times 10^{-2}$ wt. % (noble metal wt. % based on acid). When the powdered noble metal is added to the acid it immediately becomes wetted and forms a dispersion in the acid. Consequently, the supported metal is not separated from the acid after repeated extractions with hydrocarbons. However, the supported noble metal can be separated from the acid by filtration, centrifugation or other conventional methods.

While not wishing to be bound by any particular theory, it is believed that the fluoride containing acid protonates the aromatic forming a carbonium ion. Palladium then catalyzes the hydrogenation of the carbonium ion to a partially or completely saturated compound which is then cracked by the acid.

The catalyst of this invention can be utilized to hydrocrack a wide variety of hydrocarbon feedstocks, derived from naturally occurring petroleum, tar sands, bitumen, coal liquids, or shale oil liquids. Suitable feedstocks include the typical gas oil cuts (atmospheric or vacuum) cycle stocks, residua, and the like. The hydrocracking process may also be utilized to convert less complex feeds to lower molecular weight products or more tractable compounds. Thus, hydrocarbons such as benzene, toluene, xylene, anthracene, phenanthrene, pyrene, chrysene, high molecular weight paraffins (ranging to and including waxes and polymers), naphthalenes and the like may be converted in accordance with the invention.

The term "gas oil" as employed in the art includes a variety of petroleum stocks. As utilized herein, this term, unless further modified, includes any fraction distilled from petroleum which has an initial boiling point of at least about 400° F. (~215° C.), a 50 percent point of at least about 500° F. (260° C.) and an end point of at least about 600° F. (~315° C.) and boiling substantially continuously between the initial boiling point and the end point. The exact boiling range of a gas oil accordingly will be determined by the initial boiling point, the 50 percent point, and by the end point. In practice, petroleum distillations have been effected under vacuum at temperatures as high as 1200° F. (695° C.), corrected to atmospheric pressure. Accordingly, in the broad sense, a gas oil is a petroleum fraction which boils substantially continuously within an approximate range of 400° F. (215° C.) to 1200° F. (645° C.), the 50 percent point being at least about 500° F. (260° C.). Thus, a gas oil may boil over the entire approximate range of 400° F. (215° C.) to 1200° F. (645° C.) or over an intermediate range such as 500° F. (260° C.) to 900° F. (480° C.).

A residual stock is any fraction which is not distilled. Accordingly, any fraction, regardless of its initial boiling point, which includes heavy bottoms, such as tars, asphalts, etc., is a residual fraction. A residual stock may be the portion of the crude remaining undistilled at about 1200° F. (645° C.) or it may be made up of a gas oil fraction plus the portion undistilled at about 1200° F.

The refractory cycle stocks are cuts of cracked stocks which boil above the gasoline boiling range usually between about 400° F. (215° C.) and about 850° F. (450° C.). The refractory cycle stocks can be charged to the process of this invention, together with a fresh petroleum charge stock or the refractory cycle stocks may be charged to the process alone.

The hydrocracking reaction may be carried out in bulk, that is, in the absence of any solvent or in the presence of a solvent or diluent material. Useful solvent or diluent compositions include fluorinated acids and/or acid anhydrides, HF, etc. Hydrogen fluoride is the preferred reaction diluent. When a solvent or diluent is used, sufficient amounts are employed to maintain the viscosity of the reaction mixture at a desired level. Typically, from about 0.10 to 50, preferably from about 0.1 to 20 volume and more preferably about 0.3 to 5 volumes of solvent or diluent are used per volume of hydrocarbon feedstock.

Hydrocracking in accordance with the present invention is carried out at a temperature in the range of 0° to 600° C., preferably in the range of 20° to 300° C. Most preferably, the reaction is conducted at a temperature between 60° to 200° C. The hydrocracking reaction is preferably conducted at a pressure sufficient to maintain the hydrocarbon feedstock and catalyst in substantially the liquid phase. In general, the hydrogen partial pressures in the reaction zone will vary from about 25 to 3000, preferably from about 100 to 1000 psig. Typically, from 0.01 to 5.0 moles, preferably from 0.05 to 2.0 moles, of hydrogen per mole of hydrocarbon feedstock are present in the reaction zone, depending upon reactor size. The reaction time will depend upon the temperature employed, the nature of the feedstock and the products desired and, thus, may vary widely. In most cases, the reaction time will be within the range of 0.5 minute to 50 hours, preferably within the range of 1 to 250 minutes.

Hydrogen employed in the hydrocracking of the feedstock may be derived from any suitable source. Typically, in a refinery operation, the hydrogen employed may be a crude or an impure hydrogen stream such as that obtained from a naphtha reforming operation. Alternatively, hydrogen may be generated in situ by introducing hydrogen donors into the reaction zone during the course of the reaction. Examples of useful hydrogen donors include materials such as decalin, isobutane, methylcyclohexane and the like. Most preferably, elemental hydrogen is introduced into the reaction zone.

In a typical refinery operation, the process feedstock, hydrogen and optional solvent are mixed with the catalyst in a substantially liquid phase operation. The contacting may be carried out in a plurality of serially connected mixing zones. In this type of operation, the catalyst phase and hydrocarbon phase are separated, for example by settling, following reaction and the product recovered from unreacted feedstock utilizing conventional distillation techniques.

Except when sulfur containing feedstocks are used the amount of metal halide catalyst component present in the reaction zone is not always critical. Typically, from about 0.001 to 10, preferably 0.01 to 5.0 weight parts of metal halide are present in the reaction zone per weight part of feedstock. When sulfur impurities or aromatics (excluding toluene or benzene) are present in the feedstock, it is desirable, if maximum catalyst activity is desired, to have a molar excess of metal fluoride present in the reaction zone relative to the amount of sulfur poison (sulfur-containing compounds) or aromatics present in the reaction zone at any point in time. Sulfur and sulfur-containing compounds are believed to form complexes with the metal fluoride catalyst constituent and the palladium. An equilibrium is established between the amount of sulfur complex formed and the amount of sulfur in the hydrocarbon phase. Accordingly, not all of the sulfur present reacts with or complexes with the metal halide catalyst constituent and the iridium. Further, the complex formation reaction appears to be reversible via an equilibrium or reaction in that the concentration of sulfur in the acid phase can be diminished when the catalyst is contacted with a sulfur-free feedstock. In an operation wherein a support catalyst is used, the reaction liquid hourly space velocity (the liquid volume of feed per hour per volume of catalyst) would be maintained at levels of less than about 200, usually between about 0.1 and 20.

If maximum catalyst activity is desired, the feedstocks, diluents, and individual catalyst constituents should be purified prior to use to remove the majority of the sulfur compounds, water. The presence of small amounts of water are tolerable if the corresponding catalyst loss or drop in catalyst activity can be accepted. Preferably, the water concentration within the reaction zone should not exceed about 0.01 wt. %, preferably not more than about 10 wppm, based on total feed. Most preferably, the reaction is conducted in the substantial absence of water.

Unless otherwise specified, all the following examples were carried out utilizing the general procedures described in Example 1 below. Analysis of the samples and products was done using a combination of distillation and gas chromatography. The following examples illustrate the composition of the catalyst, reactants and products.

EXAMPLE 1

HYDROCRACKING 400°-700° F. b.p. FEED WITH HF/TaF$_5$ 34.5 g. of a 400°-700° F. b.p. hydrocrackate (82 ppm sulfur, 17.5 ppm nitrogen, 45% paraffins and naphthenes, 55% aromatics) 46.5 g. (2.34 mole) hydrogen fluoride and 55.2 g. (0.200 mole) tantalum pentafluoride were added to a 300 cc Hasteloy-C autoclave. The autoclave was pressured to 500 psig with hydrogen and heated to 80° C. at which the total pressure was maintained at 700-900 psig using hydrogen. As the reaction proceeded the autoclave was cooled periodically to vent any hydrocarbon gases that were formed. At these times fresh feed was also added. Hydrocracking of the feed was monitored by measuring the hydrogen consumption. While good conversion was observed for the first batch of feed very little was observed for the second and none for the third. The temperature was increased from 80°-140° C., to little avail, during the reaction in order to increase the reaction rate. After 51 hours the hydrocarbon layer was separated from the acid layer. The remaining acid layer was treated with ice. The oil which separated from the resultant two phase solution was combined with the other hydrocarbon products to yield 78.5 g. of oil.

| Reaction Time (hrs.) | Temp. Range (° C) | Feed Added(g) | Hydrogen Consumption millimoles/hr. |
|---|---|---|---|
| 0 | — | 34.5 | — |
| 6 | 80 | 34.5 | 22 |
| 27 | 70-100 | — | 2.9 |
| 46.5 | 120 | 34.5 | 4.7 |
| 51 | 140 | — | 0 |

This experiment demonstrates that the acid HF/TaF$_5$ exhibits good hydrocracking activity for the first batch of feed, but is rapidly deactivated by succeeding batches. Evidence of this is obtained from hydrogen consumption column which indicates that the reaction ceased after the second recycle.

EXAMPLE 2

HYDROCRACKING 400-700° F. b.p. FEED WITH HF/TaF$_5$-Pt/C

In a 300 cc Hasteloy-C autoclave was placed 1.83 g. of 5% Pt/C, 34.5 g of the 400°-700° F. b.p. hydrocrackate 46.9 g (2.34 moles) hydrogen fluoride, and 55.2 g (0.200 mole) tantalum fluoride. The mixture was pressured up with hydrogen and heated to 80° C. A similar reaction procedure was followed as in the earlier experiment. The hydrogen pressure was maintained between 300-1000 psig throughout the reaction. The reaction product was worked up to yield 300.2 g of oil. See analysis below:

| ° F. | wt. % feed boiling in range | wt. % 300.2 g of product boiling in range |
|---|---|---|
| <0 | — | 0.7 |
| 0-400 | — | 41.1 |
| 400-700 | 7.0 | 58.3 |
| >700 | 93.0 | |

| Reaction | Temperature | Feed Added, | Hydrocarbon | Hydrogen Consumption |

-continued

| Time,hrs. | Range, °C | g | Samples,g | millimoles/hour |
|---|---|---|---|---|
| 0 | — | 34.5 | — | — |
| 5 | 80–90 | 34.5 | — | 38 |
| 23 | 80–90 | 34.5 | — | 23 |
| 26 | 100 | 34.5 | 55.4 | 50 |
| 30 | 100 | 34.5 | 28.0 | 49 |
| 47 | 80 | 34.5 | 31.8 | 11 |
| 50 | 110 | 34.5 | 35.2 | 63 |
| 53 | 110 | 34.5 | 33.8 | 66 |
| 55 | 120 | 34.5 | — | 95 |
| 71 | 80 | — | 70.1 | 21 |

This experiment demonstrates that adding Pt/C to the HF/TaF$_5$ hydrocracking catalyst increases the acid's activity by a factor of 1.7 and its life indefinitely. The increase in catalyst activity is determined by dividing the hydrogen consumption in the first hour in this experiment by the hydrogen consumption in the first hour in Example 1. Evidence for catalyst life is the continued hydrogen consumption after eight recycles. In Example 1 hydrogen consumption stopped after 2 recycles.

EXAMPLE 3

HYDROCRACKING 400°–700° F. b.p. FEED WITH HF/TaF$_5$-Pd/C

In a 300 cc Hasteloy-C autoclave was placed 1.0 g 5% Pd/C, 34.5 g of the 400°–700° F. b.p. hydrocrackate, 45.8 g (2.29 moles) hydrogen fluoride, and 55.2 g (0.200 moles) tantalum pentafluoride. Hydrogen was pressured in and the mixture was heated to 80° C. and the same procedure was followed as in the previous experiment. The hydrogen pressure was maintained between 300–900 psig throughout the reaction. The final hydrocarbon product was separated from the acid as in the previous experiment and added to the gas and liquid samples to yield 244 g of a light oil. See analysis below:

| °F. | wt. % of feed boiling in range | wt. % of 244 g. product boiling in range |
|---|---|---|
| <0 | 0 | 1.6 |
| 0–400 | 7.0 | 62.1 |
| 400–700 | 93.0 | 36.3 |

| Reaction Time,hrs. | Temperature Range, °C. | Feed Added, g | Hydrocarbon Samples,g | Hydrogen Consumption millimoles/hours |
|---|---|---|---|---|
| 0 | — | 34.5 | — | — |
| 1.5 | 80 | 34.5 | — | 188 |
| 9 | 80–90 | 34.5 | — | 30 |
| 23 | 90 | 34.5 | 47.2 | 14 |
| 31 | 90–110 | 34.5 | 25.2 | 17 |
| 47 | 110 | 34.5 | 29.4 | 14 |
| 55 | 110–120 | 34.5 | 28.3 | 30 |
| 75 | 100 | 34.5 | 33.0 | 11 |
| 79 | 130 | — | 32.9 | 24 |

This experiment demonstrates that adding Pd/C to the HF/TaF$_5$ hydrocracking catalyst increases the acid's activity by a factor of 8.5 (determined by comparing the hydrogen consumption in the first hour for this experiment to that of Example 1). The catalyst lifetime was extended indefinitely. After seven recycles the HF/TaF$_5$-Pd/C System was still active while the HF/TaF$_5$ system, Example 1, lost its activity after two recycles.

EXAMPLE 4

HYDROCRACKING 300°–600° F. b.p. FEED WITH HF/BF$_3$-Pd/C

In a 300 cc Hasteloy-C autoclave was placed 1.0 g 5% Pd/C, 51.0 g. of a 300°–600° F. b.p. (58 ppm sulfur, 43 ppm nitrogen, 71.45% paraffins and naphthenes, 28.55% aromatic) hydrocrackate, 44.8 (2.24 moles) hydrogen fluoride, and 17.6 g (0.259 mole) of boron trifuloride. The mixture was pressured up with hydrogen and heated to 130° C. A similar reaction procedure was followed as in the earlier experiments. The hydrogen pressure was maintained between 500–1000 psig throughout the reaction. The reaction product was worked up to yield 281.6 g of oil. See analysis below:

| °F. | wt. % feed boiling in range | wt. % 281.6 g. product boiling in range |
|---|---|---|
| <180 | 0.78 | 22.9 |
| 180–400 | 5.00 | 29.6 |
| 400–600 | 94.22 | 27.5 |

| Reaction Time,hrs. | Temperature Range °C. | Feed Added, g | Hydrocarbon Samples,g | Hydrogen Consumption millimoles/hour |
|---|---|---|---|---|
| 0 | — | 51.0 | — | — |
| 1.5 | 130 | 51.0 | — | 91 |
| 3.5 | 130 | 51.0 | 43.7 | 57 |
| 5.8 | 130 | 51.0 | 46.7 | 48 |
| 21 | 30–100 | 51.0 | 47.8 | 9 |
| 24 | 130 | 51.0 | 49.8 | 52 |
| 25.5 | 130 | — | 49.1 | 81 |

This experiment demonstrates that the superacid-noble metal system, of HF/BF$_3$/Pd/C, is an active hydrocracking catalyst that is not deactivated by successive recycles.

EXAMPLE 5

EFFECT OF A NOBLE METAL HYDROGENATION CATALYST ON HF/TaF$_5$ HYDROCRACKING OF ANTHRACENE

A series of experiments were carried out to determine the effect of adding a noble metal hydrogenation catalyst to a superacid hydrocracking catalyst. All the experiments were carried out in a 300 cc Hasteloy-C autoclave which was charged with 1.0 g of 5% of the respective noble metal on carbon, 17.8 (0.100 mole) anthracene, 103 ml normal pentane, 44–66 g (2.2-2.3 moles) hydrogen fluoride, and 55.2 g (0.20 moles) tantalum pentafluoride. The mixture was pressured up with hydrogen and heated to 80° C. for 6 hours. The course of the reaction was monitored by measuring hydrogen consumption and periodically analyzing the hydrocarbon layer by gas chromatography. Throughout the reaction the hydrogen pressure was maintained at 500–600 psig. After the reaction was over all the materials boiling greater than 150° C. were separated and analyzed by gas chromatography, and nuclear magnetic resonance spectroscopy. The products from the palladium experiment were also characterized by mass spectroscopy and carbon/hydrogen analysis.

| Metal 1.0 g 5%/C | Hydrogen Consumption moles | Products | |
|---|---|---|---|
| | | heavy | light |

| Metal | Hydrogen Consumption | Products | |
|---|---|---|---|
| 1.0 g 5%/C | moles | heavy | light |
| none | 0.37 | 10.0 g anthracene | 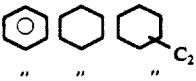 $C_2$ |
| Pt | 0.57 | 8.6 g anthracene | " " " |
| Ru | 0.45 | 10.0 g anthracene | " " " |
| Rh* | 0.56 | 8.9 g anthracene | " " " |
| Pd | 1.0 | 8.7 g completely hydrogenated anthracene | " " " |

* reaction temperature = 90° C., reaction time = 3 hrs.

These experiments demonstrate that the noble metals Pt, Ru and Rh have very little effect on the hydrogen consumption and the type of products produced when anthracene is hydrocracked with the superacid HF/TaF$_5$. On the other hand, palladium leads to a large increase in hydrogen consumption and produces an entirely different heavy product.

EXAMPLE 6

ACID CATALYZED NOBLE METAL HYDROGENATIONS

A number of experiments were carried out to demonstrate the synergism observed between HF based superacids and palladium during hydrocracking reactions. Since the purpose of the palladium in the hydrocracking reactions as to hydrogenate the aromatics in the feed, the present reactions were run at low temperatures so that the effects on hydrogenation could be unambiguously observed. This is because the cracking reactions are not observed at these temperatures. All the experiments were run in a 300 cc Hasteloy-C autoclave which was charged with the respective metal on carbon, 12.0 g (0.100 mole) mesitylene, the acid, and a partial pressure of 400 psig hydrogen. Hydrogen was replenished as it was consumed. The time to saturate one half the aromatic was obtained from the rate and quantity of hydrogen consumed, and this time was compared to the time to saturate half of the mesitylene by the respective noble metal in the absence of any acid. After the reaction was completed the product was added to ice and separated. It was analyzed by gas chromatography and nuclear magnetic resonance spectroscopy to confirm the extent of hydrogenation and the formation of trimethylcyclohexane.

| Experiment | Noble Metal 5%/C, g | Acid, g | Rate increase for acid catalyzed reactions (t½ acid-noble metal hydrogenation ÷ t½ noble metal hydrogenation) |
|---|---|---|---|
| 3317-65 | None | HF/TaF$_5$, 48/55.2 | 0 |
| 3317-69 | Pd/C, 1.0 | HF, 46 | 144 |
| 3797-109 | Pd/C, 1.0 | HF/BF$_3$, 46/0.229 | 3600 |
| 3317-67 | Pd/C, 1.0 | HF/TaF$_5$, 46/55.2 | 2500 |
| 3317-59 | Pt/D, 1.83 | HF/TaF$_5$, 48/55.2 | 16 |
| 3317-100 | Rh/C, 0.97 | HF/TaF$_5$, 46/55.2 | 0 |
| 3317-96 | Ru/C, 0.50 | HF/TaF$_5$, 48/55.2 | 0 |
| 3317-94 | Pd/C, 1.0 | TaF$_5$, 55.2 | 0 |
| 3540-13 | Pd/C, 0.5 | HBr/AlBr$_3$, 77.5/27 | 0 |
| 3540-2 | Pd/C, 1.0 | HCl, 50.2 | 0 |
| 4293-54 | Ir/C, 1.80 | HF/TaF$_5$, 2.2/0.20 | 153 |

These experiments demonstrate that there exists a special interaction between the noble metal hydrogenation catalyst palladium and HF superacids that is not found for other noble metal hydrogenation catalysts or acids. In fact, for most systems besides the HF-Pd ones the noble metals were deactivated by the acid.

What is claimed is:

1. A hydrocracking process which comprises contacting a hydrocarbon feedstock which has an initial boiling point of at least about 215° C with hydrogen, under hydrocracking conditions, and with a substantially liquid phase acid catalyst comprised of:
   a. a metal fluoride wherein the metal is selected from the group consisting of tanalum, niobium, boron and mixtures thereof;
   b. an acid selected from the group consisting of hydrofluoric acid, C$_1$-C$_4$ trifluoroalkylsulfonic acid, and trifluoroacetic acid; and
   c. a supported palladium or iridium hydrogenation component; the acid being present in at least an equimolar ratio relative to the metal fluoride and at least a portion of the metal fluoride is dissolved in the acid, the supported palladium or iridium being dispersed in the liquid acid phase and recovering a hydrocarbon product having an average molecular weight lower than the molecular weight of the feedstock.

2. The process of claim 1 wherein the hydrocracking process is carried out at temperature ranging from about 20°-300° C.

3. The process of claim 2 wherein the metal of the metal fluoride is selected from the group consisting of tantalum, niobium and mixtures thereof and the acid is hydrofluoric acid.

4. The process of claim 3 wherein the mole ratio of acid to metal fluoride is at least 2:1.

5. The process of claim 1 wherein the moles of hydrogen per mole of hydrocarbon feedstock ranges from 0.01 to 5.0.

6. The process of claim 2 wherein the hydrogen partial pressure ranges from about 25 to 3000 psig.

7. The process of claim 2 wherein at least 0.0001 wt. %, based on acid, of the metal hydrogenation component is present on the support.

8. A hydrocracking process which comprises contacting a hydrocarbon feedstock having an initial boiling point of at least about 215° C. with hydrogen, at temperatures ranging from about 20°-300° C., and with a substantially liquid phase acid catalyst comprised of:
  a. a metal fluoride selected from the group consisting of tantalum pentafluoride, niobium pentafluoride and mixtures thereof;
  b. hydrofluoric acid; and
  c. a supported palladium or iridium hydrogenation component; the acid being present in a molar ratio of at least 2:1 based on metal fluoride and at least a portion of the metal fluoride is dissolved in the acid, the supported palladium or iridium being dispersed in the liquid acid phase and recovering a hydrocarbon product having an average molecular weight lower than the average molecular weight of the feedstock.

9. The process of claim 8 wherein the feedstock is selected from the group consisting of cycle stocks, residua and mixtures thereof.

10. The process of claim 8 wherein the hydrocracking process is carried out at temperatures ranging from about 50°-160° C. and hydrogen partial pressures ranging from about 25-3000 psig.

11. The process of claim 9 wherein the hydrogenation component is palladium on carbon.

12. The process of claim 9 wherein the feedstock is a residuum and the hydrogenation component is a supported iridium.

13. The process of claim 8 wherein the moles of hydrogen per mole of hydrocarbon feedstock ranges from 0.01 to 5.0.

14. The process of claim 8 wherein at least 0.0001 wt. %, based on acid, of the hydrogenation component is present on the support.

* * * * *